(12) United States Patent
Baras et al.

(10) Patent No.: US 9,265,821 B2
(45) Date of Patent: Feb. 23, 2016

(54) INACTIVATED DENGUE VIRUS VACCINE WITH ALUMINIUM-FREE ADJUVANT

(75) Inventors: Benoit Baras, Rixensart (BE); Dirk Gheysen, Rixensart (BE); Isabelle Solange Lucie Knott, Rixensart (BE); Jean-Paul Prieels, Rixensart (BE); Jean-Francois Toussaint, Rixensart (BE)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 13/148,741

(22) PCT Filed: Feb. 16, 2010

(86) PCT No.: PCT/EP2010/051882
§ 371 (c)(1),
(2), (4) Date: Aug. 10, 2011

(87) PCT Pub. No.: WO2010/094663
PCT Pub. Date: Aug. 26, 2010

(65) Prior Publication Data
US 2011/0318407 A1 Dec. 29, 2011

Related U.S. Application Data

(60) Provisional application No. 61/153,060, filed on Feb. 17, 2009.

(51) Int. Cl.
*C07K 14/18* (2006.01)
*A61K 39/12* (2006.01)
*A61K 39/00* (2006.01)

(52) U.S. Cl.
CPC ......... *A61K 39/12* (2013.01); *A61K 2039/5252* (2013.01); *A61K 2039/55566* (2013.01); *A61K 2039/55572* (2013.01); *A61K 2039/55577* (2013.01); *C12N 2770/24134* (2013.01)

(58) Field of Classification Search
CPC ................ A61K 38/162; A61K 39/12; A61K 2039/55577; A61K 2039/5252; A61K 2039/55572; A61K 2039/521; A61K 2039/53; A61K 2039/55566; A61K 31/00; A61K 2039/525; C12N 2770/24011; C12N 2770/24234; C12N 2710/24134; C12N 2740/11034; C12N 2740/15034; C12N 2710/16634; C12N 2710/16134; C12N 2760/16134; C12N 2760/16234; G01N 2333/18
See application file for complete search history.

(56) References Cited

U.S. PATENT DOCUMENTS

| 4,235,877 A | 11/1980 | Fullerton |
| 4,372,945 A | 2/1983 | Likhite |
| 4,436,727 A | 3/1984 | Ribi |
| 4,474,757 A | 10/1984 | Arnon et al. |
| 4,866,034 A | 9/1989 | Ribi |
| 4,877,611 A | 10/1989 | Cantrell |
| 5,057,540 A | 10/1991 | Kensil et al. |
| 4,912,094 B1 | 2/1994 | Myers et al. |
| 6,005,099 A | 12/1999 | Davies |
| 6,254,873 B1 * | 7/2001 | Putnak et al. ............. 424/218.1 |
| 6,303,347 B1 | 10/2001 | Johnson et al. |
| 6,372,227 B1 * | 4/2002 | Garcon et al. ............. 424/283.1 |
| 6,544,518 B1 * | 4/2003 | Friede et al. .............. 424/184.1 |
| 6,613,556 B1 | 9/2003 | Eckels et al. |
| 6,638,514 B1 | 10/2003 | Eckels et al. |
| 6,846,489 B1 | 1/2005 | Garcon et al. |
| 7,226,602 B2 | 6/2007 | Whitehead et al. |
| 7,323,182 B2 * | 1/2008 | Garcon et al. ............. 424/278.1 |
| 7,357,936 B1 * | 4/2008 | Garcon ....................... 424/278.1 |
| 7,399,472 B2 * | 7/2008 | Friede et al. .............. 424/184.1 |
| 2006/0183224 A1 | 8/2006 | Aerts et al. |
| 2007/0031451 A1 | 2/2007 | Slifka et al. |
| 2007/0191314 A1 * | 8/2007 | Klucker et al. ............ 514/102 |
| 2008/0279926 A1 | 11/2008 | Vandepapeliere |
| 2010/0158946 A1 * | 6/2010 | Moriyama et al. ........ 424/218.1 |
| 2011/0150914 A1 * | 6/2011 | Shresta et al. ............. 424/186.1 |

FOREIGN PATENT DOCUMENTS

| EP | 0 109 942 B1 | 10/1991 |
| EP | 0 729 473 B1 | 8/2000 |
| EP | 0 362 279 B1 | 5/2008 |
| WO | WO 94/21292 A1 | 9/1994 |
| WO | WO 96/11711 A1 | 4/1996 |
| WO | WO 96/33739 A1 | 10/1996 |
| WO | WO 98/50399 A1 | 11/1998 |
| WO | WO 00/57907 | 10/2000 |
| WO | WO 00/58444 | 10/2000 |
| WO | WO 03/011223 A2 | 2/2003 |
| WO | WO 03/099195 A2 | 12/2003 |
| WO | WO 2007/068907 A2 | 6/2007 |
| WO | WO 2008/043774 A1 | 4/2008 |

OTHER PUBLICATIONS

Putnak et al. J. Infect. Dis. Dec. 1996, vol. 174 (6), pp. 1176-1184.*
Bomford et al., "Adjuvanticity and ISCOM formation by structurally diverse saponins", *Vaccine*, 10(9):572-577(1992).
Kensil, "Saponins as vaccine adjuvants", *Critical Reviews™ in Therapeutic Drug Carrier Systems*, 13 (1-2):1-55 (1996).
Lacaille-Dubois, et al., "A review of the biological and pharmacological activities of saponins", *Phytomedicine* 2:63-386 (1996).
Leroux-Roels, et al., "Antigen sparing and cross-reactive immunity with an adjuvanted rH5N1 prototype pandemic influenza vaccine: a randomised controlled trial", *The Lancet*, 370(9587):580-589 (2007).
Li, et al., "Characterization of antibody responses elicited by human immunodeficiency virus type 1 primary isolate trimeric and monomeric envelope glycoproteins in selected adjuvants", *Journal of Virology*, 80(3):1414-1426 (2006).

(Continued)

*Primary Examiner* — Bao Li
(74) *Attorney, Agent, or Firm* — Haiyan Chen; William Majarian

(57) ABSTRACT

The present disclosure provides immunogenic compositions for the prevention and/or treatment of disease caused by dengue virus.

19 Claims, 4 Drawing Sheets

(56) References Cited

OTHER PUBLICATIONS

Pichichero, "Improving vaccine delivery using novel adjuvant systems", *Human Vaccines*, 4(4):262-270 (2008).
Putnak, et al., "An evaluation of dengue type-2 inactivated, recombinant subunit, and live-attenuated vaccine candidates in the rhesus macaque model", *Vaccine*, 23(35):4442-4452 (2005).
SIGMA: "TiterMax Classic Adjuvant", XP007913247 Retrieved from the Internet: URL:http://www.sigmaaldrich.com/etc/medial/ib/docs/Sigma/Datasheet/2/h4397dat.Par.0001.File.tmp/h4397dat.pdf> [retrieved on May 28, 2010] (2006).
Vandepapeliere, et al., "Vaccine adjuvant systems containing monophosphoryl lipid A and QS21 induce strong and persistent humoral and T cell responses against hepatitis B surface antigen in healthy adult volunteers", *Vaccine*, 26(10):1375-1386 (2008).
Whitehead, et al., "Prospects for a dengue virus vaccine", *Nature Reviews*, 5(7):518-528 (2007).
Allison et al. New Generation Vaccines, ed Graeme C. Woodrow and. Myron M. Levine, copyright 1990. Chapter title: Adjuvants for a New Generation of Vaccines. p. 129-140.
Nishizawa et al. "Efficient Syntheses of a Series of Trehalose Dimycolate (TDM)/Trehalose Dicorynomycolate (TDCM) Analogues and Their Interleukin-6 Level Enhancement Activity in Mice Sera" J. Org. Chem.: 72 (5), pp. 1627-1633 (2007).

* cited by examiner

ICS Day 21 - restimulation with PIV Den-2 (10 μg/ml)

| | Den-2 (200ng) Plain | Den-2 (200ng) AS22A | Den-2 (2μg) AS04D/2 | Den-2 (2μg) AS03B | Den-2 (2μg) AS01E | PBS |
|---|---|---|---|---|---|---|
| CD4+IL2+ | 0.03 | 0.16 | 0.10 | 0.22 | 0.78 | 0.03 |
| CD4+IL2+INFg+ | 0.035 | 0.04 | 0.05 | 0.03 | 0.83 | 0.01 |
| CD4+INFg+ | 0.04 | 0.03 | 0.03 | 0.04 | 0.67 | 0.01 |

% Den-2 specific CD4+ T cells

FIG. 4.

INACTIVATED DENGUE VIRUS VACCINE WITH ALUMINIUM-FREE ADJUVANT

CROSS-REFERENCE TO RELATED APPLICATIONS

This application is the national stage of international patent application no. PCT/EP2010/051882, filed 16 Feb. 2010, which claims benefit of the earlier filing date of U.S. provisional application No. 61/153,060, filed 17 Feb. 2009, the disclosures of which are incorporated herein by reference.

BACKGROUND

Dengue is an acute viral disease of man which is transmitted by mosquitos. It is endemic in the tropics and subtropics, worldwide, where an estimated 100,000,000 cases occur annually Although relatively rare, dengue hemorrhagic fever (DHF) and dengue shock syndrome (DSS) are significant causes of death in children. At present, there is no vaccine to protect against dengue and attempts to prevent disease by controlling the mosquito vector have proven largely ineffective. Thus, there remains a need for a safe and effective vaccine to protect against disease caused by dengue virus.

BRIEF SUMMARY

The present disclosure concerns compositions that elicit an immune response against dengue virus. More specifically, this disclosure concerns inactivated dengue virus vaccines that include an adjuvant. The compositions disclosed herein include an aluminum-free adjuvant, for example, an aluminum-free adjuvant capable of promoting a Th1 immune response. Methods for their use, e.g., in the formulation of medicaments, for prevention of treatment of disease caused by Dengue virus are also described.

BRIEF DESCRIPTION OF THE DRAWINGS

FIG. 4 is a bar graph illustrating a characterization of the cellular immune response by intracellular cytokine staining in peripheral blood cells.

DETAILED DESCRIPTION

Introduction

Figure 1:
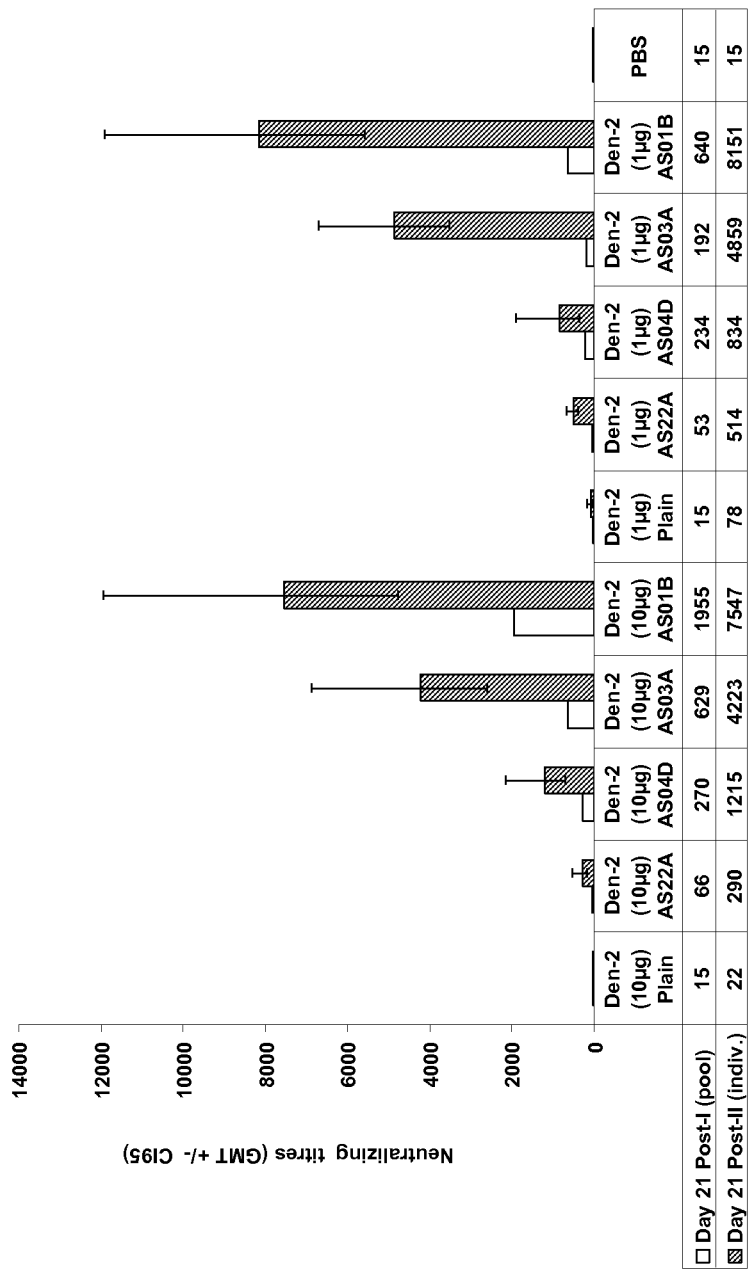
FIG. 1 is a bar graph illustrating Anti-Den-2 neutralizing antibody titres in naïve C57B1/6 mice.

The present invention is directed to a vaccine that satisfies the need for a safe and effective dengue vaccine. Purified inactivated dengue virus vaccine has a major advantage over live-attenuated dengue virus in that inactivated viruses are not infectious and therefore, can not revert to virulence or cause disease. One potential drawback of a purified inactivated dengue virus vaccine as compared to a live-attenuated is a reduced capacity to induce high titers of dengue specific neutralizing antibodies and the relatively short duration of the protective immune response. These drawbacks are overcome by the formulation of the purified inactivated dengue antigen with an appropriate adjuvant. As disclosed herein, the adjuvant is an aluminum-free (alum-free) adjuvant (or adjuvant system) that effectively elicits high titers of dengue-specific neutralizing antibodies. In an embodiment, the adjuvant elicits a predominantly Th1 response or a balanced Th1/Th2 response characterized by production of interferon gamma (IFN-γ).

The immunogenic compositions disclosed herein include at least one (that is, one or more than one) inactivated dengue virus antigen, in combination with an aluminum-free adjuvant. The inactivated dengue virus antigen can be selected from a Dengue-1 virus antigen, a Dengue-2 virus antigen, a Dengue-3 virus antigen and a Dengue-4 virus antigen. Thus, the immunogenic composition can be a monovalent composition including a single inactivated dengue virus antigen from a single strain selected from Dengue-1, Dengue-2, Dengue-3 or Dengue-4, or the composition can be a multivalent (e.g., bivalent, trivalent, tetravalent) composition containing inactivated antigens of more than one of these dengue strains. In one exemplary embodiment, the immunogenic composition includes a Dengue-2 virus antigen. For example, the immunogenic composition can be a monovalent composition that contains an inactivated Dengue-2 antigen. Alternatively, the immunogenic composition can be a bivalent, trivalent or tetravalent composition that contains an inactivated Dengue-2 virus antigen in combination with one, two or three additional inactivated dengue virus antigens. For example, in one embodiment, the composition is a tetravalent composition that includes an inactivated Dengue-1 virus antigen, an inactivaed Dengue-2 virus antigen, an inactivaed Dengue-3 virus antigen and an inactivaed Dengue-4 virus antigen.

The one or more inactivated dengue virus antigens are formulated with an adjuvant that is free of aluminum or aluminum salts, that is, an aluminum-free adjuvant or adjuvant system. In one embodiment, the adjuvant includes an oil-in-water emulsion. For example, the oil-in-water emulsion can include an oil phase that incorporates a metabolisable oil, and optionally includes an additional oil-phase component, such as a tocol. The oil-in-water emulsion also contains an aqueous component, such as a buffered saline solution (e.g., phosphate buffered saline). In addition, the oil-in-water emulsion typically contains an emulsifier. In one embodiment, the metabolizable oil is squalene. In one embodiment, the tocol is alpha-tocopherol. In one embodiment, the emulsifier is a nonionic surfactant emulsifier (such as polyoxyethethylene sorbitan monooleate, TWEEN80™). In exemplary embodiments, the oil-in-water emulsion contains squalene and alpha tocopherol in a ratio which is equal or less than 1 (w/w).

In one specific example, the immunogenic composition includes an oil-in-water emulsion adjuvant system formulated in a dose comprising: from about 2% to about 10% squalene; from about 2% to about 10% alpha-tocopherol; and from about 0.3% to about 3% polyoxyethethylene sorbitan monooleate For example, the immunogenic composition can include an adjuvant formulated in a dose comprising: from about 10 mg to about 12 mg squalene; from about 10 mg to about 12 mg alpha-tocopherol; and from about 4 mg to about 6 mg polyoxyethethylene sorbitan monooleate. In one specific example, the adjuvant includes in a single (whole) dose: 10.68 mg squalene; 11.86 mg tocopherol; 4.85 mg polyoxyethethylene sorbitan monooleate. In other embodiments, the immunogenic composition is formulated with a fractional dose (that is a dose, which is a fraction of the preceding single dose formulations, such as one half of the preceding quantity of components, ¼ of the preceding quantity of components, or another fractional dose, e.g., ⅓, ⅙, etc.) of the preceding quantity of components.

In certain embodiments, the inactivated dengue virus antigen is formulated with an alum-free adjuvant system that includes 3-Deacylated monophosphoryl lipid A (3D-MPL) and/or QS21. In one embodiment, the adjuvant system includes 3D-MPL and QS21. For example, in one embodiment, the adjuvant contains 3D-MPL and QS21 in a liposomal formulation. Optionally, the adjuvant system also contains cholesterol. In one specific embodiment, the adjuvant includes QS21 and cholesterol. Optionally, the adjuvant system contains 1,2-Dioleoyl-sn-Glycero-3-phosphocholine (DOPC). For example, in one specific adjuvant system to be formulated with the inactivated dengue virus antigen contains cholesterol, DOPC, 3D-MPL and QS21.

In one specific example, the immunogenic composition includes an adjuvant formulated in a dose that includes: from about 0.1 to about 0.5 mg cholesterol; from about 0.25 to about 2 mg DOPC; from about 10 μg to about 100 μg 3D-MPL; and from about 10 μg to about 100 μg QS21. In one embodiment, the ratio of cholesterol to QS21 in the adjuvant is 5:1 (w/w). For example, the ratio of cholesterol to QS21 in the adjuvant can be approximately or exactly 1:1 (w/w). In one specific formulation, the adjuvant is formulated in a single dose that contains: about 0.25 mg cholesterol; about 1.0 mg DOPC; about 50 μg 3D-MPL; and about 50 μg QS21. In other embodiments, the immunogenic composition is formulated with a fractional dose (that is a dose, which is a fraction of the preceding single dose formulations, such as one half of the preceding quantity of components (cholesterol, DOPC, 3D-MPL and QS21), ¼ of the preceding quantity of components, or another fractional dose, e.g., ⅓, ⅙, etc.) of the preceding quantity of components.

In another aspect, this disclosure concerns a method for producing a dengue vaccine comprising the following steps: providing at least one purified inactivated dengue virus antigen; and, formulating the at least one purified inactivated dengue virus antigen with an aluminum-free adjuvant. For example, the immunogenic composition can be formulated with a whole virus antigen produced from either a virulent or attenuated strain, which has been inactivated or killed. For example, the live (virulent or attenuated) virus can be killed or inactivated, rendering it incapable of replication, using chemical agents, such as formaldehyde, betapropiolactone (BPL), or hydrogen peroxide, or using ultraviolet irradiation, or by using a combination of two or more inactivation steps (which can be the same or different, e.g., formaldehyde and BPL, formaldehyde and UV irradiation, BPL and UV irradiation, hydrogen peroxide and BPL, hydrogen peroxide and UV irradiation, etc., in any combination). Optionally, the inactivated dengue virus is subjected to additional processing, such as splitting, or further purification of antigenic subunits.

In another aspect, this disclosure concerns a method for preventing, ameliorating or treating disease caused by dengue virus in a subject comprising: administering an immunogenic composition (e.g., vaccine) containing at least one inactivated dengue virus antigen in combination with an alum-free adjuvant (as described herein). In one embodiment, the method involves administering the immunogenic composition to a child, such as a child under 5 years or age, or under 1 year of age. In one embodiment, the immunogenic composition is administered to a naïve subject under 1 year of age. In other embodiments, the immunogenic composition is administered to an adult subject, such as an adult subject, such as an elderly subject over about 60 or 65 years of age. Such subjects can be previously exposed to dengue virus. Typically, the vaccine is administered parentally, e.g., intramuscularly. In another aspect, this disclosure concerns an immunogenic composition containing at least one purified inactivated dengue virus antigen in combination with an alum-free adjuvant for use in medicine, e.g., for the prevention, ameleioration or treatment of Dengue virus infection and/or Dengue virus induced disease, such as hemorrhagic fever (DHF) and dengue shock syndrome (DSS).

TERMS

In order to facilitate review of the various embodiments of this disclosure, the following explanations of terms are provided. Additional terms and explanations can be provided in the context of this disclosure.

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

An "immunogenic composition" is a composition of matter suitable for administration to a human or animal subject (e.g., in an experimental setting) that is capable of eliciting a specific immune response, e.g., against a pathogen, such as dengue virus. As such, an immunogenic composition includes one or more antigens (for example, whole purified virus or antigenic subunits, e.g., polypeptides, thereof) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or treated, e.g., reduced or ameliorated) by inhibiting replication of the pathogen (e.g., dengue virus) following exposure of the subject to the pathogen. In the context of this disclosure, the term immunogenic composition will be understood to encompass compositions that are intended for administration to a subject or population of subjects for the purpose of eliciting a protective or palliative immune response against dengue (that is, vaccine compositions or vaccines).

The term "purification" (e.g., with respect to a pathogen or a composition containing a pathogen) refers to the process of removing components from a composition, the presence of which is not desired. Purification is a relative term, and does not require that all traces of the undesirable component be removed from the composition. In the context of vaccine production, purification includes such processes as centrifugation, dialization, ion-exchange chromatography, and size-exclusion chromatography, affinity-purification or precipitation. Thus, the term "purified" does not require absolute purity; rather, it is intended as a relative term. Thus, for example, a purified virus preparation is one in which the virus is more enriched than it is in its generative environment, for instance within a cell or population of cells in which it is replicated naturally or in an artificial environment. A preparation of substantially pure viruses can be purified such that the desired virus or viral component represents at least 50% of the total protein content of the preparation. In certain embodiments, a substantially pure virus will represent at least 60%, at least 70%, at least 80%, at least 85%, at least 90%, or at least 95% or more of the total protein content of the preparation.

An "isolated" biological component (such as a virus, nucleic acid molecule, protein or organelle) has been substantially separated or purified away from other biological components in the cell and/or organism in which the component occurs or is produced. Viruses and viral components, e.g., proteins, which have been "isolated" include viruses, and proteins, purified by standard purification methods. The term also embraces viruses and viral components (such as viral proteins) prepared by recombinant expression in a host cell.

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule).

In the context of the present disclosure, a dengue virus antigen is typically a whole killed or inactivated virus. The term "inactivated" in the context of a dengue virus vaccine means that the antigenic component (e.g., virus) is incapable of replication in vivo or in vitro. For example, the term inactivated encompasses a virus that has been replicated, e.g., in vitro, and then killed using chemical or physical means such that it is no longer capable of replicating. The term can also include antigens produced by further processing (e.g., splitting, fractionation, and the like), and components produced by recombinant means, e.g., in cell culture.

An "adjuvant" is an agent that enhances the production of an antigen-specific immune response as compared to administration of the antigen in the absence of the agent. Common adjuvants include aluminum containing adjuvants that include a suspensions of minerals (or mineral salts, such as aluminum hydroxide, aluminum phosphate, aluminum hydroxyphosphate) onto which antigen is adsorbed. In the context of the present disclosure the adjuvants are aluminum-(alum-)free adjuvants, which are formulated in the absence of any such aluminum salts. Alum-free adjuvants include oil and water emulsions, such as water-in-oil, and oil-in-water (and variants therof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

An "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

A "Th1" biased immune response is characterized by the presence of CD4+ T helper cells that produce IL-2 and IFN-γ, and thus, by the secretion or presence of IL-2 and IFN-γ. In contrast, a "Th2" biased immune response is characterized by a preponderance of CD4+ helper cells that produce IL-4, IL-5, and IL-13.

A "subject" is a living multi-cellular vertebrate organism. In the context of this disclosure, the subject can be an experimental subject, such as a non-human animal, e.g., a mouse, a cotton rat, or a non-human primate. Alternatively, the subject can be a human subject.

The immunogenic compositions disclosed herein are suitable for preventing, ameliorating and/or treating disease caused by infection with dengue virus.

The immunogenic compositions disclosed herein include one or more purified inactivated dengue virus antigen. For example, the immunogenic compositions can include a single strain of dengue virus (i.e., a monovalent composition), or they can contain more than one strain of dengue virus (i.e., a multivalent composition). Typically, a multivalent composition contains strains selected from different serotypes. Because there are four serotypes of dengue virus which can cause disease, that is, dengue type one (DEN-1), dengue type two (DEN-2), dengue type three (DEN-3) and dengue type four (DEN-4), and because cross-reactive non-neutralizing antibodies are predisposing to more severe forms of dengue disease, one representative of each serotype can be selected for inclusion into the final vaccine in order to guarantee protection against disease from any of the four serotypes. Thus, in one embodiment, the immunogenic composition is a tetravalent composition that includes strains selected from each of the four serotypes of dengue virus.

The viruses used as antigens can be selected from essentially any strain (or strains) of dengue virus. For example, a virus strain can be selected for each serotype, which is chosen based on its conformity to a defined (e.g., consensus) sequence for the serotype, such as a DEN-1 consensus sequence, a DEN-2 consensus sequence, a DEN-3 consensus sequence, or a DEN-4 consensus sequence. Such a virus can be naturally occurring or synthetic. Alternatively, a virus strain can be selected to correlate with a strain prevalent in the area or population in which the vaccine is intended to be administered. Another option is to select strains for each serotype as a matter of convenience based on availability or prior experience. For example, exemplary strains are described in U.S. Pat. No. 6,254,873, which is incorporated by reference herein. Additional suitable strains are disclosed, e.g., in U.S. Pat. No. 7,226,602. Additional strains can be found, for example, in the VBRC viral genome database (http://athena.bioc.uvic.ca/organisms/Flaviviridae/Dengue/Curated_genes), and the Dengue Virus Database (http://www.broad.mit.edu/annotation/viral/Dengue/ProjectInfo.html).

In the context of a purified inactivated dengue virus vaccine, either virulent or attenuated strains can be used. Typically virulent strains propagate to higher titer in host cells, facilitating production at commercial scale. However, virulent strains require special care in handling to prevent infection of personnel involved in manufacturing. Attenuated strains, e.g., developed by adaptation to production in cultured cells and selection for reduced virulence and/or reduced replication in the mosquito vectors of dengue, require fewer handling precautions but can be difficult to produce. Exemplary attenuated strains suitable for use in the context of an immunogenic composition containing an inactivated dengue virus and an aluminum-free adjuvant are described in WO 00/57907 and U.S. Pat. No. 6,638,514, and WO 00/58444 and U.S. Pat. No. 6,613,556, which are incorporated herein by reference. Thus, the strain(s) selected are typically chosen from among the numerous strains available to replicate in cells that are suitable for production of materials intended for human use (e.g., cells that are certified free of pathogens). For example, strains can be screened to identify those viruses that grow to the highest titers, for example from a titer of at least about $5\times10^6$ pfu/ml, preferably at least $1\times10^7$ pfu/ml or more in the cell line(s) of choice; (ii) selecting those strains of dengue virus which grow to the highest titers in the cell line(s) of choice; and (iii) further adapting those selected strains for enhanced growth by additional passage from one to several times in the cell line(s) of choice. The selected viruses (for example, chosen from the four serotypes of dengue viruses) can be further adapted to grow to high titers by additional cell culture passages or by genetic manipulation to make high-titered master and production seed lots.

Suitable cell lines for propagating dengue virus include mammalian cells, such as Vero cells, AGMK cells, BHK-21 cells, COS-1 or COS-7 cells, MDCK cells, CV-1 cells, LLC-MK2 cells, primary cell lines such as fetal Rhesus lung (FRhL-2) cells, BSC-1 cells, and MRC-5 cells, or human diploid fibroblasts, as well as avian cells, chicken or duck embryo derived cell lines, e.g., AGE1 cells, and primary, chicken embryo fibroblasts, and mosquito cell lines, such as C6/36. Preferably, the chosen cell(s) are adapted to grow in the absence of serum or serum-derived proteins, and can maintain dengue virus replication at high titers under serum-free (and/or protein-free) growth conditions.

To propagate virus in cell culture, the selected dengue virus strain is used to infect the host cell (for example, selected from among the suitable cell types listed above). After virus adsorption, the cultures are fed with medium capable of supporting growth of the cells. Preferably, the medium does not contain serum or serum-derived proteins or other animal-derived proteins, or serum-free mediva can be used to replace serum-containing media during production. Numerous formulations of serum-free medium are available commercially. A detailed description of methods for producing virus in cells maintained under serum-free conditions can be found, for example, in published US Patent Application No. 20060183224, which is incorporated herein by reference.

The host cells are maintained in culture for several days until the desired virus titer is achieved. Optionally, the cells are maintained in a continuous perfusion system from which virus can be intermittently or continuously obtained over the course of several days or more. Under non-continuous culture conditions, a virus titer of at least about $10^6$ to $10^7$ PFU/ml by 3-7 days post infection, is desirable. In some host cells, the titer remains high for several days, and virus can be recovered at multiple timepoints to maximize yield. For example, virus can be harvested from these cultures daily, from about 3 to about 13 days post infection by collecting the supernates and refeeding the cells. Optionally, the supernates can be pooled prior to additional processing. In other host cells, virus can be grown to a higher titer, but over a shorter period of time. In such a case, the virus can be harvested at peak titer as determined empirically.

For example, Vero cells can be amplified in VPSFM medium with Ficin up to passage 141. One additional passage can be performed in the presence of porcine trypsin. Cells can be seeded at approximately $0.7\times10^6$ cells/ml in a Bioreactor (4 L) and cultivated on micro-carriers (cytodex-1) for 5 days in VPSFM+ Pluronic 0.1% under perfusion conditions (e.g., D0→: 0 Volume/day; D1→D2: 1 v/d; then 1.5 v/d for the 3 next days). Cells at approximately $3\times10^6$ cells/ml are then infected (at 35° C.) with dengue virus, e.g., at a MOI 0.01 in DMEM+Glutamine 4 mM++FBS 2% for 2 h with a reduced medium volume (2 L) at 37° C. The medium volume in the Bioreactor is then adjusted to 4 L. After 3 days, a large part of the medium (around 3 L) is removed and replaced by DMEM medium+Glutamin 4 mM. At 7 days post-infection, virus can be harvested.

To recover virus, the virus is harvested by common methods known in the art including slow-speed centrifugation (for example at 1500×g for 10 min), or by filtration through a filter of pore size of 0.45 μm. Methods for concentrating said virus(es) are within the scope of a person with ordinary skill in the art and include, for example, ultrafiltration (e.g., with a membrane of no greater than 300 kDa pore size), or precipitation with polyethelene glycol (PEG) 8000. Methods for purifying viruses are known to a person with ordinary skill in the art and include continuous or multi-step sucrose gradients, purification by column chromatography using size exclusion, ion exchange, adsorption, or affinity columns, or purification by partitioning in polymer two-phase or multi-phase systems, and any combination thereof. Methods for assaying for virus positive fractions include plaque assay, hemagglutination (HA) assay, and/or antigen assays such as immunoassays.

For example, dengue virus can be concentrated from culture supernate by polyethylene glycol (PEG) precipitation. Supernate fluids from infected cells are clarified by centrifugation (1,500×g) for 10 min. The clarified supernate is adjusted to 6% PEG 8000 (Sigma) and 0.5 M NaCl and held at 4° C. with gentle stirring for 45 min. The precipitate is collected by centrifugation at 5000×g for 50 min and resuspended in STE buffer (0.1 M NaCl, 10 mM tris, 1 mM EDTA, pH 7.6). The virus suspension can then be clarified by centrifugation (12,000×g for 10 min at 4° C.). The pellet is discarded, and the supernate is then centrifuged (170,000×g, 80 min, 4° C.) to pellet virus. This virus pellet is resuspended in STE buffer at the desired concentration.

Alternatively, or additionally, dengue virus can be concentrated from cell supernates by tangential flow ultrafiltration. Supernate fluids from infected cells is clarified by centrifugation at low speed as described above, then filtered through a 0.45 μm CN filter (Nalgene). The filtered supernate is concentrated by tangential flow ultrafiltration using a low-protein-binding 100 kDa-cutoff membrane (e.g., omega 100 K screen channel, Filtron, Inc.). Concentration is carried out at 4° C. using a flow rate of 400 ml per min, a filtration rate of approximately 100 ml per min and a pressure of 20-30 psi.

Further purification can be achieved using sucrose gradient ultracentrifugation. Dengue virus can be purified on sucrose gradients essentially as described previously (Srivastava et al. *Arch. Virol.* 96: 97-107, 1987) with minor modifications. Fifteen ml sucrose gradients can be made in 1"×3.5" (40 ml) ultracentifuge tubes (ULTRA-CLEAR™, Beckman, Inc.) by stepwise addition of the following w/w sucrose solutions in phosphate buffered saline, pH 7.4 (PBS, without Ca and Mg, Whittaker MA Bioproducts): 2 ml 60%, 2 ml 55%, 2 ml 50%, 2 ml 45%, 2 ml 40%, 2 ml 35%, 2 ml 30% and 1 ml 15%. A smooth gradient is formed by allowing the tubes to stand for 2-4 hrs at room temperature. Up to 25 ml of concentrated virus is applied to each tube. Ultracentrifugation is then carried out in (e.g., in a SW 28 rotor (Beckman) at 17,000 rpm for 18 hrs at 4° C.). Following centrifugation, 1 to 2 ml fractions can be collected from the bottom of the tubes. Fractions can be assayed for total protein, virus HA, and virus antigen as desired. Positive gradient fractions are typically pooled, and diluted to 10% or less sucrose with Medium 199 (M199, Gibco-BRL) or PBS. Optionally, prior to inactivation, virus pools can be filtered through a 0.22 μm low-protein-binding filter (GV type, Millipore).

Following purification, the recovered viruses are inactivated by a means selected to preserve their antigenicity and immunogenicity while destroying their infectivity. In one example, an effective quantity of an agent, such as formalin or beta.-propriolactone is added to the virus, and the mixture is incubated with the inactivating agent until inactivated. For example, formalin (37% formaldehyde) is diluted 1:40 in PBS, and the pH is adjusted to approximately 7.4 with 1 N NaOH. The solution is then sterilized by passage through a 0.22 μm CN filter (Nalgene). This formalin solution is added to purified virus (1:50) for a final formalin concentration of 0.05%. Inactivation is carried out at between 15 and 25° C., for 48 hrs up to 14 days (typically, 10 days or less). Optionally, virus is filtered through a 0.22 μm GV type filter and transferred to a fresh container. At the completion of inactivation, free formalin in the bulk culture is neutralized, e.g., by addition of an equimolar amount of sterile 10% w/v sodium bisulfite.

Alternatively, inactivation can be achieved by irradiating the virus with a radioactive source until the virus is inactivated. One favorable example of a radioactive source is cobalt-60, at doses sufficient to inactivate the infectivity of the viruses while preserving the antigenicity essentially intact. Examples of useful doses are those which fall within the range from 5.5 to 7.0 Mrads. For example, virus aliquots of 50 μl in 1.5 ml sterile polypropylene tubes are frozen and placed on dry ice in the gamma cell of a $^{60}$Co source, for a period sufficient to deliver the desired irradiation.

Alternatively, ultraviolet irradiation can be employed to inactivate dengue virus. Suitable devices for ultraviolet irradiation of virus in a commercial setting are well known in the art, and devices are commercially available, e.g., from Bayer, which expose the supernate (or other fluid containing the virus) to a UV-C light source at approximately 254 nm, for a time sufficient to inactivate virus while preserving immunogenicity.

Alternatively, the dengue virus can be inactivated using hydrogen peroxide as described, e.g., in published US Patent Application No. 20070031451, which is incorporated herein by reference.

If desired, two or more activation steps can be employed. When two or more inactivation steps are employed the steps can be the same or different. For example, a combination of any suitable inactivation process, such as any of the preceding inactivation processes, can be employed during the purification and inactivation of dengue virus for formulation into an immunogenic composition for administration to a human subject.

Quality of the virus preparation can be monitored by a variety of methods known in the art. For example, virus can be monitored prior to inactivation in a plaque titration assay. Virus is amplified on the same or a different host cell as used for production, and used to infect a suitable cell line, such as LLC-MK2 cells or Vero cell monolayers, and the number of viral plaques can be assessed to determine infectivity of the recovered virus (see, e.g., Sukhavachana et al. *WHO Bull.* 35: 65-6, 1966). Another method for assessing quantity and quality of recovered antigen is by virus hemagglutination (HA) and hemagglutination-inhibition (HI) assays. Virus HA and HI assays can be performed as previously described (Clarke & Casals, *Am. J. Trop. Med. Hyg.* 7: 561-73, 1958). Total protein is determined essentially as described by Bradford (*Anal. Biochem.* 72: 248, 1976), using a commercially-available kit (BioRad, Hercules, Calif.) and bovine serum albumin (BSA) or gamma globulin as a standard.

Alternatively, antigen can be detected and/or quantitated after inactivation, e.g., in an antigen spot blot assay. To detect and quantitate antigen in inactivated virus preparations virus samples are diluted out serially, typically by two-fold dilution, and spotted onto nitrocellulose paper. The papers are air-dried, blocked with 5% casein in PBS, and incubated with a specific antibody or antiserum followed by enzyme-linked secondary antibody. Virus can also be detected by western blotting. In brief, antigen preparations are solubilized in SDS-PAGE sample buffer containing 1% SDS, 66 mM Tris-HCl, pH 6.8, 1% glycerol and 0.7% bromphenol blue at 22 C. for 10 min and electrophoresed on 12.5% polyacrylamide gels (e.g., as described by Feighny et al. *Am. J. Trop. Med. Hyg.* 50(3): 322-8, 1994). Resolved proteins are transferred electrophoretically to nylon or nitrocellulose membrane. Proteins can then be detected by staining with colloidal gold and viral antigens can be identified immunologically using a non-isotopic modification of the Western blot procedure.

IMMUNOGENIC COMPOSITIONS AND METHODS

The inactivated dengue virus(es) is mixed with a suitable aluminum-free adjuvant to produce an immunogenic composition suitable for immunizing human subjects in order to elicit high titers of virus neutralizing antibodies and protect the immunized human from disease caused by dengue virus. Typically, the inactivated dengue virus(es) are formulated in a pharmaceutically acceptable carrier or excipient.

Pharmaceutically acceptable carriers and excipients are well known and can be selected by those of skill in the art. For example, the carrier or excipient can favorably include a buffer. Optionally, the carrier or excipient also contains at least one component that stabilizes solubility and/or stability.

Examples of solubilizing/stabilizing agents include detergents, for example, laurel sarcosine and/or polyoxyethylene sorbitan monooleate. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in *Remington's Pharmaceutical Sciences*, by E. W. Martin, Mack Publishing Co., Easton, Pa., 5th Edition (1975).

Accordingly, suitable excipients and carriers can be selected by those of skill in the art to produce a formulation suitable for delivery to a subject by a selected route of administration.

Suitable excipients include, without limitation: glycerol, Polyethylene glycol (PEG), Sorbitol, Trehalose, N-lauroyl-sarcosine sodium salt, L-proline, Non detergent sulfobetaine, Guanidine hydrochloride, Urea, Trimethylamine oxide, KCl, $Ca^{2+}$, $Mg^{2+}$, $Mn^{2+}$, $Zn^{2+}$ and other divalent cation related salts, Dithiothreitol, Dithioerytrol, and β-mercaptoethanol. Other excipients can be detergents (including: polyoxyethylene sorbitan monooleate, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide).

The immunogenic compositions disclosed herein also include an adjuvant. In the context of an immunogenic composition suitable for administration to a subject for the purpose of eliciting a protective immune response against dengue, the adjuvant is an aluminum-free adjuvant selected to elicit a balanced Th1/Th2 response or a Th1 biased immune response. Such an immune response is characterized by the production of γ-IFN.

The adjuvant is typically selected to enhance a balanced Th1/Th2 response or a Th1 biased immune response in the subject, or population of subjects, to whom the composition is administered. For example, when the immunogenic composition is to be administered to a subject of a particular age group susceptible to (or at increased risk of) dengue infection, the adjuvant is selected to be safe and effective in the subject or population of subjects. Thus, when formulating an immunogenic composition containing an inactivated dengue virus antigen for administration in neonatal, or infant subjects (such as subjects between birth and the age of one year), or in a child (e.g., such as subjects between birth and five years of age), the adjuvant is selected to be safe and effective in neonates and infants and/or children.

Additionally, the adjuvant is typically selected to enhance a Th1 immune response when administered via a route by which the immunogenic composition is administered. For example, when the immunogenic composition is formulated for intramuscular administration, adjuvants including one or more of 3D-MPL, squalene (e.g., QS21), liposomes, and/or oil and water emulsions are favorably selected.

One suitable adjuvant for use in combination with inactivated dengue antigens is a non-toxic bacterial lipopolysaccharide derivative. An example of a suitable non-toxic derivative of lipid A, is monophosphoryl lipid A or more particularly 3-Deacylated monophoshoryl lipid A (3D-MPL). 3D-MPL is sold under the name MPL by GlaxoSmithKline Biologicals N.A., and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB2220211 A. Chemically it is a mixture of 3-deacylated monophosphoryl lipid A with 3, 4, 5 or 6 acylated chains. In the compositions of the present invention small particle 3D-MPL can be used. Small particle 3D-MPL has a particle size such that it can be sterile-filtered through a 0.22 μm filter. Such preparations are described in WO94/21292.

A lipopolysaccharide, such as 3D-MPL, can be used at amounts between 1 and 100 μg per human dose of the immunogenic composition. Such 3D-MPL can be used at a level of about 50 μg, for example between 40-60 μg, suitably between 45-55 μg or between 46 and 54 μg or between 47 and 53 μg or between 48 and 52 μg, or between 49 and 51 μg, or at 50 μg. In another embodiment, for example for administration to an infant or child, the dose of the immunogenic composition comprises a fractional dose of 3D-MPL at a level of about 25 μg per human dose of the immunogenic composition. Such 3D-MPL can be used at a level of about 25 μg, for example between 20-30 μg, suitably between 21-29 μg or between 22 and 28 μg or between 23 and 27 μg or between 24 and 26 μg, or 25 μg. In other embodiment (e.g., suitable for administration to very young infants), the human dose of the immunogenic composition comprises an a fractional dose containing an even lower amount of 3D-MPL at a level of about 10 μg, for example between 5 and 15 μg, suitably between 6 and 14 μg, for example between 7 and 13 μg or between 8 and 12 μg or between 9 and 11 μg, or 10 μg. In a further embodiment, the human dose of the immunogenic composition comprises 3D-MPL at a level of about 5 μg, for example between 1 and 9 μg, or between 2 and 8 μg or suitably between 3 and 7 μg or 4 and μg, or 5 μg.

In other embodiments, the lipopolysaccharide can be a β(1-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references. Nonetheless, each of these references is incorporated herein by reference. In addition to the aforementioned immunostimulants (that are similar in structure to that of LPS or MPL or 3D-MPL), acylated monosaccharide and disaccharide derivatives that are a sub-portion to the above structure of MPL are also suitable adjuvants. In other embodiments, the adjuvant is a synthetic derivative of lipid A, some of which are described as TLR-4 agonists, and include, but are not limited to: OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-D-glucopyranosyldihydrogenphosphate), (WO 95/14026); OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO 99/64301 and WO 00/0462); and OM 197 MP-Ac DP (3S-,9R)-3-(R)-dodecanoyloxytetradecanoylamino]-4-oxo-5-aza-9-[(R)-3-hydroxytetradecanoylamino] decan-1,10-diol, 1-dihydrogenophosphate 10-(6-aminohexanoate) (WO 01/46127).

Other TLR4 ligands which can be used are alkyl Glucosaminide phosphates (AGPs) such as those disclosed in WO 98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR4 agonists, and some are TLR4 antagonists. Both are thought to be useful as adjuvants.

Other suitable TLR-4 ligands, capable of causing a signaling response through TLR-4 (Sabroe et al, JI 2003 p1630-5) are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, and muramyl dipeptide (MDP). In one embodiment the TLR agonist is HSP 60, 70 or 90. Other suitable TLR-4 ligands are as described in WO 2003/011223 and in WO 2003/099195, such as compound I, compound II and compound III disclosed on pages 4-5 of WO2003/011223 or on pages 3-4 of WO2003/099195 and in particular those compounds disclosed in WO2003/011223 as ER803022, ER803058, ER803732, ER804053, ER804057, ER804058, ER804059, ER804442, ER804680, and ER804764. For example, one suitable TLR-4 ligand is ER804057.

Other adjuvants that can be used in immunogenic compositions with an inactivated dengue virus antigens, e.g., alternatively to, or in combination with, 3D-MPL, or another adjuvant described herein, are saponins, such as QS21.

Saponins are taught in: Lacaille-Dubois, M and Wagner H. (1996). A review of the biological and pharmacological activities of saponins Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree *Quillaja Saponaria Molina*), and fractions thereof, are described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739, and U.S. Pat. No. 6,846,489). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1, which are incorporated herein by reference. Such saponins, or fractions thereof, can be used alone or in combination, and optionally can be formulated as ISCOMS. Other saponins which have been used in systemic vaccination studies include those derived from other plant species such as *Gypsophila* and *Saponaria* (Bomford et al., Vaccine, 10(9):572-577, 1992).

QS21 is an Hplc purified non-toxic fraction derived from the bark of *Quillaja Saponaria Molina*. A method for producing QS21 is disclosed in U.S. Pat. No. 5,057,540. Non-reactogenic adjuvant formulations containing QS21 are described in WO 96/33739. The aforementioned references are incorporated by reference herein. Said immunologically active saponin, such as QS21, can be used in amounts of between 1 and 50 µg, per human dose of the immunogenic composition. Advantageously QS21 is used at a level of about 1 and 100 µg per human dose of the immunogenic composition. For example, QS21 can be used at a level of about 50 µg, for example between 40-60 µg, suitably between 45-55 µg or between 46 and 54 µg or between 47 and 53 µg or between 48 and 52 µg, or between 49 and 51 µg, or at 50 µg. In another embodiment, for example for administration to an infant or child, the dose of the immunogenic composition comprises a fractional dose 25 µg, for example between 20-30 µg, suitably between 21-29 µg or between 22-28 µg or between 23-27 µg or between 24-26 µg, or 25 µg. In another embodiment, the human dose of the immunogenic composition comprises QS21 at a level of about 10 µg, for example between 5 and 15 µg, suitably between 6-14 µg, for example between 7-13 µg or between 8-12 µg or between 9-11 µg, or 10 µg. In a further embodiment, the human dose of the immunogenic composition comprises QS21 at a level of about 5 µg, for example between 1-9 µg, or between 2-8 µg or suitably between 3-7 µg or 4-6 µg, or 5 g. Such formulations comprising QS21 and further comprising cholesterol (suitably in a liposomal formulation) have been shown to be successful Th1 stimulating adjuvants when formulated together with an antigen. Thus, for example, an inactivated dengue virus antigen can favorably be employed in immunogenic compositions with an adjuvant comprising a combination of QS21 and cholesterol. Optionally such an adjuvant also contains 1,2-Dioleoyl-sn-Glycero-3-phophocholine (DOPC). Saponins, such as QS21, can also be formulated with one or more additional immunostimulating agents (such as 3D-MPL as discussed herein, or e.g., CpG oligonucleotides, or other TLR agonists).

Combinations of different adjuvants, such as those mentioned hereinabove, can also be used in compositions with inactivated dengue virus antigens. For example, as already noted, QS21 can be formulated together with 3D-MPL. The ratio of QS21:3D-MPL will typically be in the order of 1:10 to 10:1; such as 1:5 to 5:1, and often substantially 1:1. Typically, the ratio is in the range of 2.5:1 to 1:1 3D-MPL:QS21. Optionally, the combination of QS21 and 3D-MPL also contains one or both of cholesterol and DOPC. Additional details regarding formulations and dosages of such combinations, especially doses (fractional doses) suitable for administration to infants and children, can be found in WO2007068907 and US 20080279926, which are incorporated herein by reference. When formulated in combination, this combination can enhance an antigen-specific Th1 immune response.

In some instances, the adjuvant formulation includes an oil-in-water emulsion.

One example of an oil-in-water emulsion comprises a metabolisable oil, such as squalene, a tocol such as a tocopherol, e.g., alpha-tocopherol, and a surfactant, such as polysorbate 80 or TWEEN™ 80, in an aqueous carrier, and does not contain any additional immunostimulants(s). The aqueous carrier can be, for example, phosphate buffered saline. One favorable example of such an oil-in-water emulsion is designated herein AS03. Additionally the oil-in-water emulsion can contain sorbitan trioleate (SPAN™ 85) and/or lecithin and/or tricaprylin. Another example of an oil-in-water emulsion is MF59, which is a squalene based emulsion system sold by Novartis Vaccine and Diagnostics.

In another embodiment of the invention there is provided a vaccine composition comprising an antigen or antigen composition and an adjuvant composition comprising an oil-in-water emulsion, wherein said oil-in-water emulsion comprises 0.25-10 mg metabolisable oil (suitably squalene), 0.25-11 mg tocol (suitably a tocopherol, such as alpha-tocopherol) and 0.125-4 mg emulsifying agent. In some instances, e.g., for administration to children, the oil-in-water emulsion is present in a fractional dose of ½, ¼, or ⅛ of the standard adult dose. Additional details regarding fractional doses of oil-in-water emulsions suitable for use in combination with an inactivated dengue virus vaccine can be found in WO 2008043774, U.S. Ser. No. 12/445,090, which is incorporated herein by reference.

In particular formulations using an oil-in-water emulsion, such an emulsion can include additional components, for example, such as cholesterol, squalene, alpha tocopherol, and/or a detergent, such as polyoxyethethylene sorbitan monooleate (TWEEN™ 80) or sorbitan trioleate. In exemplary formulations, such components can be present in the following amounts: from about 1-50 mg cholesterol, from 2 to 10% squalene, from 2 to 10% alpha tocopherol and from 0.3 to 3% polyoxyethethylene sorbitan monooleate (all volume/volume). Typically, the ratio of squalene:alpha tocopherol is equal to or less than 1 as this provides a more stable emulsion. In some cases, the formulation can also contain a stabilizer.

Optionally, the oil and water emulsion adjuvant includes one or more further immunostimulant. In one specific embodiment, the adjuvant formulation includes 3D-MPL prepared in the form of an emulsion, such as an oil-in-water emulsion. In some cases, the emulsion has a small particle size of less than 0.2 µm in diameter, as disclosed in WO 94/21292. For example, the particles of 3D-MPL can be small enough to be sterile filtered through a 0.22 micron membrane (as described in European Patent number 0 689 454). Alternatively, the 3D-MPL can be prepared in a liposomal formulation. Optionally, the adjuvant containing 3D-MPL (or a derivative thereof) also includes an additional immunostimulatory component.

For example, when an immunogenic composition with an inactivated dengue virus antigen is formulated for administration to an infant, the dosage of adjuvant is determined to be effective and relatively non-reactogenic in an infant subject. Generally, the dosage of adjuvant in an infant formulation is lower than that used in formulations designed for administration to adult (e.g., adults aged 65 or older). For example, the amount of 3D-MPL is typically in the range of 1 µg-200 µg, such as 10-100 µg, or 10 µg-50 µg per dose. An infant dose is typically at the lower end of this range, e.g., from about 1 µg to about 50 µg, such as from about 2 µg, or about 5 µg, or about 10 µg, to about 25 µg, or to about 50 µg. Typically, where QS21 is used in the formulation, the ranges are comparable (and according to the ratios indicated above). For adult and elderly populations, the formulations typically include more of an adjuvant component than is typically found in an infant formulation.

An immunogenic composition typically contains an immunoprotective quantity (or a fractional dose thereof) of the antigen and can be prepared by conventional techniques. Preparation of immunogenic compositions, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

Typically, the amount of antigen in each dose of the immunogenic composition is selected as an amount which induces an immunoprotective response without significant, adverse side effects in the typical subject. Immunoprotective in this context does not necessarily mean completely protective against infection; it means protection against symptoms or disease, especially severe disease associated with the virus. The amount of antigen can vary depending upon which specific immunogen is employed. Generally, it is expected that each human dose will comprise 0.05-100 µg of inactivated virus, such as from about 0.1 µg (e.g., 0.1, 0.2, 0.3, 0.4, or 0.5 µg) to about 50 µg, for example, from about 0.5 µg to about 30 µg, such as about 1 µg, about 2 µg, about 3 µg, about 4 µg, about 5 µg, about 10 µg, about 15 µg, about 20 µg, or about 25 µg, of each strain of inactivated dengue virus. The amount utilized in an immunogenic composition is selected based on the subject population (e.g., infant). An optimal amount for a particular composition can be ascertained by standard studies involving observation of antibody titres and other responses in subjects. Following an initial vaccination, subjects can receive a boost after a suitable interval (e.g., in about 4 weeks).

It should be noted that regardless of the adjuvant selected, the concentration in the final formulation is calculated to be safe and effective in the target population. For example, immunogenic compositions for eliciting an immune response against dengue virus in humans are favorably administered to infants (e.g., infants between birth and 1 year, such as between 0 and 6 months, at the age of initial dose). Immunogenic compositions for eliciting an immune response against dengue are also favorably administered to adult humans (e.g., alone or in a combination with antigens of other pathogens for example in the context of a "traveler's" vaccine). It will be appreciated that the choice of adjuvant can be different in these different applications, and the optimal adjuvant and concentration for each situation can be determined empirically by those of skill in the art.

Methods for eliciting an immune response against dengue in a subject are also a feature of this disclosure. Such methods include administering an immunologically effective amount of a composition comprising an inactivated dengue virus antigen and an aluminum-free adjuvant to a subject, such as a human subject. For example, the composition includes an adjuvant that elicits a Th1 biased immune response. The composition is formulated to elicit an immune response specific for dengue, that is, the composition is formulated to, and results in, a Th1 biased immune response that reduces or prevents infection with dengue virus and/or reduces or prevents a pathological response following infection with a dengue virus.

Typically, vaccines are prepared as injectables, either as liquid solutions or suspensions; solid form suitable for solution in, or suspension in, liquid prior to injection may also be prepared. Although the composition can be administered by a variety of different routes, most commonly, the immunogenic compositions are delivered by an intramuscular, subcutaneous or intradermal route of administration. Generally, the vaccine may be administered subcutaneously, intradermally, or intramuscularly in a dose effective for the production of neutralizing antibody and protection. The vaccines are administered in a manner compatible with the dosage formulation, and in such amount as will be prophylactically and/or therapeutically effective. The quantity to be administered, which is generally in the range of 0.05-100 µg of each strain of inactivated virus per dose, depends on the subject to be treated, capacity of the subject's immune system to synthesize antibodies, and the degree of protection desired. Precise amounts of the vaccine to be administered may depend on the judgment of the practitioner and may be peculiar to each subject.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months or years. The dosage regimen will also, at least in part, be determined by the need of the individual and be dependent upon the judgment of the practitioner. Examples of suitable immunization schedules include: a first dose, followed by a second dose between 7 days and 6 months, and an optional third dose between 1 month and two years post initial immunization, or other schedules sufficient to elicit titers of virus-neutralizing antibodies expected to confer protective immunity, for example selected to correspond to an established pediatric vaccine schedule. The generation of protective immunity against dengue with an inactivated virus vaccine may reasonably be expected after a primary course of immunization consisting of 1 to 3 inoculations. These could be supplemented by boosters at intervals (e.g., every two years) designed to maintain a satisfactory level of protective immunity.

EXAMPLES

Example I

Immunogenicity of Exemplary Immunogenic Compositions that Contain a Dengue Purified Inactivated Virus (1 µg and 10 µg) and an Aluminum-Free Adjuvant Groups of 15 naïve adult female C57B1/6 mice were vaccinated intramuscularly with two doses of an exemplary vaccine candidate containing purified inactivated virus (PIV) of a Dengue-2 (Den-2) strain. The vaccine was administered in a total volume of 50 µl. Mice were immunized with formulations containing Dengue PIV alone or formulations containing Dengue PIV vaccine adjuvanted with Alum (alum hydroxide), 3-Deacylated monophosphoryl lipid A (3D-MPL) adsorbed onto aluminum hydroxide (AS04D), an oil-in-water emulsion (ASO3A), and 3D-MPL and QS21 in a liposomal formulation (AS01B) (see groups in Table 1 below). AS03A and AS01B are two non-limiting examples of aluminum (alum)-free adjuvants. The Dengue PIV antigen used for formulation was a purified bulk obtained essentially as described herein from a culture of a wild-type Den-2 virus, inactivated with 0.185% of formalin for 7 days at 22° C.

Throughout the examples described herein, statistical analyses were performed on post vaccination CD4+ frequencies and neutralizing titres by UNISTAT. The protocol applied for analysis of variance can be briefly described as follow; Log transformation of data; Shapiro-Wilk test on each population (group) in order to verify the normality of groups distribution; Cochran test in order to verify the homogenicity of variance between the different populations (groups); Analysis of variance on selected data; Test for interaction of one-way ANOVA; Tukey-HSD Test for multiple comparisons.

TABLE 1

| Gr | Antigen/Formulation | PIV Den-2 (Conc Total prot/dose) | Other treatment |
|---|---|---|---|
| 1 | PIV Den-2 Plain (non-adjuvanted) | 10 µg | Days 0 and 21 |
| 2 | PIV Den-2 + AS22A (Al(OH)3) | 10 µg | Days 0 and 21 |
| 3 | PIV Den-2 + AS04D | 10 µg | Days 0 and 21 |
| 4 | PIV Den-2 + AS03A | 10 µg | Days 0 and 21 |
| 5 | PIV Den-2 + AS01B | 10 µg | Days 0 and 21 |
| 6 | PIV Den-2 + Plain (non-adjuvanted) | 1 µg | Days 0 and 21 |
| 7 | PIV Den-2 + AS22A (Al(OH)3) | 1 µg | Days 0 and 21 |
| 8 | PIV Den-2 + AS04D | 1 µg | Days 0 and 21 |
| 9 | PIV Den-2 + AS03A | 1 µg | Days 0 and 21 |
| 10 | PIV Den-2 + AS01B | 1 µg | Days 0 and 21 |
| 11 | PBS | | Days 0 and 21 |

The humoral immune response was measured 21 days after the first immunization (set as Day 0) and the second immunization (Day 21), that is, on days 21 and 42, post immunization. Serum samples were tested using an anti-Dengue neutralization assay. In brief, to measure mouse serum neutralizing titers against Dengue virus, serial dilutions of filtered and heat inactivated serum were incubated with a fixed amount of monospecific Dengue virus (Dengue-2). The mixture of serum and virus was then added to a monolayer of Vero cells (from a WHO cell bank) and incubated for 4 days. Viral infection inhibition by serum samples was measured using an ELISA that detects cell-associated viral antigens on Vero cells adhered to a 96-well microplate. The resulting optical density readings were automatically processed into an Excel spreadsheet that uses a log mid-point linear regression program model to derive a virus percent reduction of infection (referred to as microneutralization 50 percent reduction, or MN50). The virus neutralization titer (MN50) is defined as the reciprocal of the serum dilution giving 50% reduction in the absorbance readout of the assay when compared to the virus dose control without serum (TV).

Neutralizing antibody titers were determined on pooled sera for each group at day 21, and on individual sera at day 42. Results are illustrated in FIG. 1. The same immunological profile was observed for both doses tested (1 and 10 µg total protein). The neutralizing antibody titers were enhanced after two administrations of 1 µg or 10 µg of Dengue PIV vaccine as compared to the response after a single dose of the composition. For both doses of Dengue PIV vaccine tested, significantly lower neutralizing antibody responses were observed with the non-adjuvanted vaccine compared to the adjuvanted Dengue PIV vaccine ($p<0.00001$). At the 10 µg dose of total protein, Dengue PIV vaccine adjuvanted with AS04D induced significantly higher neutralizing antibody response compared to the response induced by the Dengue PIV vaccine adjuvanted with alum alone (AS22A) ($p=0.0027$). No difference was observed between these two adjuvants at the dose of 1 µg total protein ($p>0.05$). As shown in FIG. 1, compositions adjuvanted with either alum-free adjuvant induced significantly higher neutralizing antibody responses (AS03A ($p<0.0173$) or AS01B ($p<0.0001$)) than did the compositions with AS04D or AS22A. Dengue PIV vaccine adjuvanted with AS03A and AS01B induced similar levels of neutralizing antibody titers ($p>0.05$).

These results demonstrate that at the dose of 1 or 10 µg total protein of Dengue PIV, higher neutralizing antibody titres were observed in mice immunized with compositions containing an adjuvant system that does not contain alum (as exemplified by AS03A or AS01B shown here) compared to the response induced by the same antigen in combination with an alum-containing adjuvant (e.g., AS22A or AS04D).

Example II

Immunogenicity of Exemplary Immunogenic Compositions that Contain a Dengue Purified Inactivated Virus (1 µg and 10 µg) and an Aluminum-Free Adjuvant at Different Dilutions of Adjuvant Groups of 15 adult female C57B1/6 mice were administered two doses of the exemplary Dengue PIV vaccine intramuscularly in a total volume of 50 µl. Mice were immunized with formulations containing either Dengue PIV alone or formulations containing Dengue PIV antigen adjuvanted with Alum (AS22A, alum hydroxide), or dilution of different adjuvant systems, e.g., such as ½ the standard dose of AS04D (AS04D/2), AS03B (oil-in-water emulsion-based Adjuvant System containing 5.93 mg tocopherol), and AS01E (half dose of AS01B) (detailed in Table 2). The PIV used for formulation was a purified bulk obtained from a culture of a wild-type Den-2 virus, inactivated with 0.185% of Formalin for 7 days at 22° C.

TABLE 2

| Gr | Antigen/Formulation | PIV Den-2 Conc Total prot/mouse | Other treatment |
|---|---|---|---|
| 1 | PIV Den-2 Plain (non-adjuvanted) | 1 µg | Days 0 and 21 |
| 2 | PIV Den-2 + AS22A (Al(OH)3) | 1 µg | Days 0 and 21 |
| 5 | PIV Den-2 + AS04D/2 | 10 µg | Days 0 and 21 |
| 6 | PIV Den-2 + AS03B | 10 µg | Days 0 and 21 |
| 7 | PIV Den-2 + AS01E | 10 µg | Days 0 and 21 |
| 8 | PIV Den-2 + AS04D/2 | 1 µg | Days 0 and 21 |
| 9 | PIV Den-2 + AS03B | 1 µg | Days 0 and 21 |
| 10 | PIV Den-2 + AS01E | 1 µg | Days 0 and 21 |
| 11 | PBS | | Days 0 and 21 |

The humoral immune response to immunization was measured 21 days after the first and second immunizations (Days 21 and 42, respectively) on 15 mice/group. Serum samples were tested by the neutralization assay described above.

Figure 2:
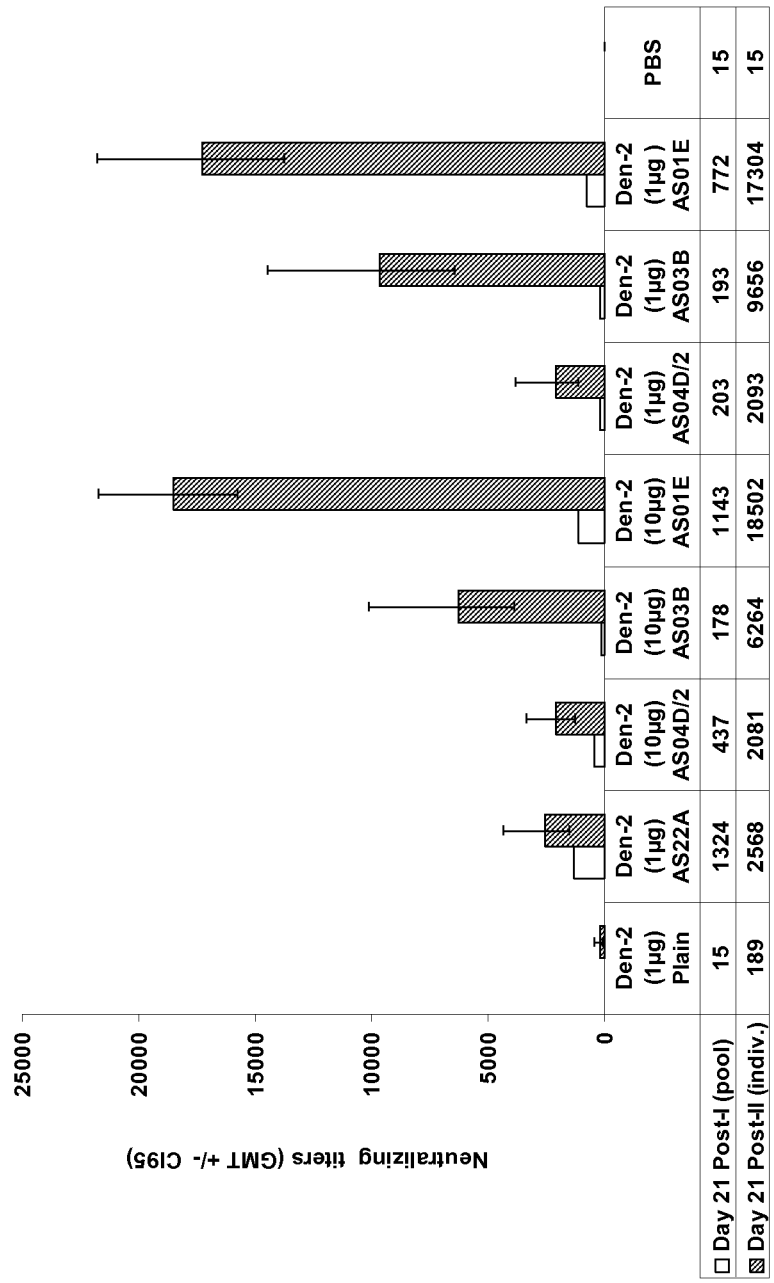
FIG. 2 is a bar graph illustrating Anti-Den-2 neutralizing antibody titres in naïve C57B1/6 mice.

Neutralizing antibody titers on pool sera per group at day 21, and on individual sera per group at day 42, are presented in FIG. 2. The same immunological profile was observed for both doses tested (1 and 10 µg total protein). Higher neutralizing antibody titers were observed after two administrations of the immunogenic composition as compared to the response induced after only a single administration of either 1 µg or 10 µg of Dengue PIV antigen. For both doses of Dengue PIV vaccine tested, significantly lower neutralizing antibody responses were observed with the non-adjuvanted vaccine compared to the adjuvanted Dengue PIV formulations (p<0.00001). At the dose of 1 µg protein total, Dengue PIV vaccine adjuvanted with AS04D/2 induced similar neutralizing antibody response compared to the response induced by the Dengue PIV vaccine adjuvanted with alum alone (p>0.05). For the same vaccine dose tested, Dengue PIV vaccine adjuvanted with AS03B or AS10E induced significantly higher neutralizing antibody titers compared to vaccine adjuvanted with AS04D (p≤0.029 for AS03B and p≤0.00001 for AS01E) or alum (p≤0.0035 for AS03B and p≤0.00001 for AS01E).

In conclusion, at a dose of either 1 or 10 µg total protein of Dengue PIV antigen, higher neutralizing antibody titres were observed in mice immunized with compositions adjuvanted with a dilution of adjuvant system that does not contain alum (AS03B or AS01E) compared to the response induced by the same antigen adjuvanted with an alum-containing adjuvant (AS22A or AS04D/2).

Example III

Immunogenicity of Exemplary Immunogenic Compositions that Contain a Dengue Purified Inactivated Virus ((2 µg and 200 ng) and an Aluminum-Free Adjuvant at Different Dilutions of Adjuvant Groups of 25 adult female C57B1/6 mice were immunized intramuscularly with two doses of an exemplary Dengue PIV vaccine in a total volume of 50 µl. Mice were immunized with formulations containing Dengue PIV antigen alone or formulations containing Dengue PIV antigen adjuvanted with Alum (AS22A, alum hydroxide) or dilution of different adjuvant, e.g., AS04D (AS04D/2), AS03B (oil-in-water emulsion-based Adjuvant System containing 5.93 mg tocopherol), and AS10E (half dose of AS01B) (the groups are detailed in Table 3). The PIV antigen used for formulation was a purified bulk obtained from a culture of a wild-type Den-2 virus, inactivated with 0.185% of formalin for 7 days at 22° C.

TABLE 3

| Gr | Antigen/Formulation | PIV Den-2 Conc Total prot/mouse | Other treatment |
|---|---|---|---|
| 1 | PIV Den-2 Plain (non-adjuvanted) | 200 ng | Days 0 and 14 |
| 2 | PIV Den-2 + AS22A (Al(OH)3) | 200 ng | Days 0 and 14 |
| 3 | PIV Den-2 + AS04D/2 | 2 µg | Days 0 and 14 |
| 4 | PIV Den-2 + AS03B | 2 µg | Days 0 and 14 |
| 5 | PIV Den-2 + AS01E | 2 µg | Days 0 and 14 |
| 6 | PIV Den-2 + AS04D/2 | 200 ng | Days 0 and 14 |
| 7 | PIV Den-2 + AS03B | 200 ng | Days 0 and 14 |
| 8 | PIV Den-2 + AS01E | 200 ng | Days 0 and 14 |
| 9 | PBS | | Days 0 and 14 |

The humoral immune response to administration of the immunogenic composition was measured 14 days after the first and second immunizations (Days 14 and 28, respectively) on 15 mice/group. Serum samples were evaluated by the neutralization assay described above.

Ten mice from each group were sacrificed at 7 days post immunization in order to evaluate the cellular immune response by ICS using 5 pools of 2 spleens each. CMI was only evaluated for the groups of mice immunized with 2 µg of Dengue PIV vaccine adjuvanted with AS04D/2, AS03B, AS01E and in mice immunized with 200 ng of the non-adjuvanted vaccine or the vaccine adjuvanted with AS22A (groups 1 to 5) and mice receiving PBS (group 9). Sera of 15 other mice were collected 14 days after the first immunization (day 14) and the second immunization (day 28).

Figure 3:
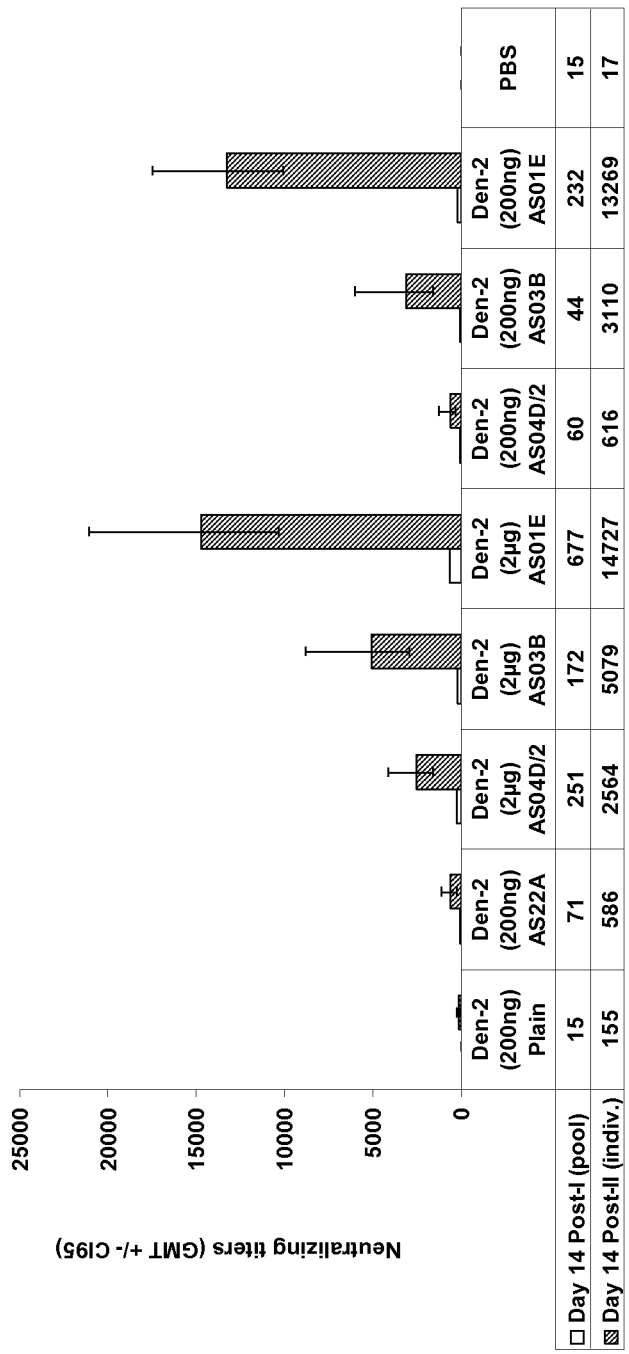
FIG. 3 is a bar graph illustrating Anti-Den-2 neutralizing antibody titres in naïve C57B1/6 mice

Neutralizing antibody titers were determined on pooled sera per group at day 14, and on individual sera per group at day 28. Results are provided in FIG. 3. Higher neutralizing antibody titers were observed after two administrations of either 2 µg or 200 ng of Dengue PIV vaccine as compared to the titers after a single administration. Significantly higher neutralizing antibody responses were observed with the adjuvanted Dengue PIV formulations as compared to the non-adjuvanted formulation (p<0.0089). At the dose of 200 ng of Dengue PIV, the formulations adjuvanted with AS03B and AS01E elicited a substantially higher neutralizing antibody response as compared to the response elicited by the same antigen formulated with AS22A or AS04D/2. At the lower dose of antigen, Dengue PIV adjuvanted with AS22A and AS04D/2 induced comparable neutralizing antibody response at the dose of 200 ng total protein (p>0.05). At the higher antigen dose of 2 µg total protein, the formulation with AS04D/2 induced similar neutralizing antibody response compared to the vaccine adjuvanted with AS03B (p>0.05). However, at lower doses of antigen (200 ng), the formulation with ASO3B elicited significantly higher neutralizing antibody titers that AS04D/2 (p=0.0012). Interestingly, Dengue PIV adjuvanted with AS10E induced significantly higher neutralizing antibody titers compared to all other groups (p≤0.0028).

The cellular immune response was also evaluated following two administrations of Dengue PIV in combination with the aforementioned dilutions of adjuvant. CD4+ T cell cytokine responses were evaluated 7 days after the second immunization (Day 21) by ICS (FIG. 4).

Lower CD4+ T cell response was induced by the non-adjuvanted Dengue PIV vaccine compared to all other groups ($p \leq 0.001$). Mice immunized with Dengue PIV vaccine adjuvanted with AS01E induced the highest CD4+ T cell responses compared to mice in all other groups ($p \leq 0.00001$). CD4+ T cells response obtained with Dengue PIV vaccine adjuvanted with AS22A, AS04D/2 and AS03B were not statistically different ($p > 0.05$).

In conclusion, higher neutralizing antibody titres were observed in mice immunized with Dengue PIV vaccine adjuvanted with an adjuvant system that does not contain alum (AS03B or AS01E) compared to the response induced by this vaccine adjuvanted with Alum hydroxide (AS22A). Of note, Dengue PIV vaccine adjuvanted with AS01E induced higher neutralizing antibody response and higher CD4 T cell response compared to the vaccine adjuvanted with the alum-containing adjuvant, AS04D/2.

In summary, as compared to mice immunized with Dengue PIV formulated with Alum-containing adjuvants (AS22A, AS04D or AS04D/2), mice immunized with a vaccine formulated with alum-free adjuvant systems (e.g., AS01B or AS01E, which do not contain alum), elicited substantially higher neutralizing antibody response and CD4+ T cell responses. These results demonstrate the favorable immunogenic attributes of Dengue PIV vaccines formulated with alum-free adjuvants.

We claim:

1. An immunogenic composition comprising at least one inactivated dengue virus antigen and an adjuvant suitable for administration to a human subject, wherein the adjuvant comprises an oil in water emulsion, and the adjuvant is aluminum-free and does not contain any of the following: i) an immunostimulatory oligonucleotide, ii) QS21 and iii) 3D-MPL, wherein said oil in water emulsion comprises a metabolisable oil, a tocol and an emulsifier.

2. The immunogenic composition of claim 1, wherein the at least one inactivated dengue virus antigen is selected from the group consisting of a Dengue-1 virus antigen, a Dengue-2 virus antigen, a Dengue-3 virus antigen and a Dengue-4 virus antigen.

3. The immunogenic composition of claim 1, wherein the at least one inactivated dengue virus antigen comprises a Dengue-2 virus antigen.

4. The immunogenic composition of claim 1, wherein the at least one inactivated dengue virus antigen is an inactivated whole dengue virus.

5. The immunogenic composition of claim 1, wherein the oil in water emulsion adjuvant comprises squalene.

6. The immunogenic composition of claim 1, wherein the tocol is alpha-tocopherol.

7. The immunogenic composition of claim 1, wherein the oil in water emulsion adjuvant comprises a nonionic surfactant emulsifier.

8. The immunogenic composition of claim 7, wherein the nonionic surfactant is polyoxyethylene sorbitan monooleate.

9. The immunogenic composition of claim 1, wherein the oil in water emulsion adjuvant is formulated in a dose comprising:
from about 2% to about 10% squalence,
from about 2% to about 10% alpha-tocopherol,
from about 0.3% to about 3% polyoxyethylene sorbitan monooleate.

10. The immunogenic composition of claim 9, wherein the oil in water emulsion adjuvant is formulated in a dose comprising:
from about 10 mg to about 12 mg squalene,
from about 10 mg to about 12 mg alpha-tocopherol,
from about 4 mg to about 6 mg polyoxyethylene sorbitan monooleate.

11. The immunogenic composition of claim 10, wherein the oil in water emulsion adjuvant is formulated in a dose comprising:
10.68 mg squalene,
11.86 mg alpha-tocopherol,
4.85 mg polyoxyethylene sorbitan monooleate.

12. The immunogenic composition of claim 9, wherein the oil in water emulsion adjuvant is formulated in a fractional dose comprising a fraction of the quantity of each of:
from about 10 mg to about 12 mg squalene,
from about 10 mg to about 12 mg alpha-tocopherol,
from about 4 mg to about 6 mg polyoxyethylene sorbitan monooleate,
wherein the fraction is selected from 1/2, 1/3, 1/4 and 1/6.

13. A method for producing a dengue vaccine comprising providing at least one purified inactivated dengue virus antigen; and formulating the at least one purified inactivated dengue virus antigen with an adjuvant suitable for administration to a human subject, wherein the adjuvant comprises an oil in water emulsion, and the adjuvant is aluminum-free and does not contain any one of the following: i) an immunostimulatory oligonucleotide, ii) QS21 and iii) 3D-MPL, wherein said oil in water emulsion comprises a metabolisable oil, a tocol and an emulsifier.

14. The immunogenic composition of claim 1, wherein the at least one inactivated dengue virus antigen is a purified inactivated whole dengue virus.

15. The immunogenic composition of claim 1 wherein the immunogenic composition comprises inactivated whole Dengue-1 virus, inactivated whole Dengue-2 virus, inactivated whole Dengue-3 virus and inactivated whole Dengue-4 virus.

16. The immunogenic composition of claim 1 wherein the immunogenic composition comprises purified inactivated whole Dengue-1 virus, purified inactivated whole Dengue-2 virus, purified inactivated whole Dengue-3 virus and purified inactivated whole Dengue-4 virus.

17. The method of claim 13, wherein the at least one purified inactivated dengue virus antigen is a whole killed virus inactivated by one or more steps of contacting or exposing a live virus to an agent selected from the group of: formaldehyde, betapropiolactone (BPL), hydrogen peroxide, ultraviolet irradiation and gamma irradiation.

18. A method for preventing, ameliorating or treating disease caused by dengue virus in a human subject comprising: administering the immunogenic composition of claim 1 to the subject.

19. The immunogenic composition of claim 2, wherein the immunogenic composition comprises a Dengue-1 virus antigen, a Dengue-2 virus antigen, a Dengue-3 virus antigen and a Dengue-4 virus antigen.

* * * * *